(12) United States Patent
Paz-Soldán

(10) Patent No.: US 7,322,367 B2
(45) Date of Patent: Jan. 29, 2008

(54) DEVICE FOR CLEANING TEETH

(76) Inventor: Luis José Paz-Soldán, Brucknerplein 16, NL-5653 ER Eindhoven (NL)

( * ) Notice: Subject to any disclaimer, the term of this patent is extended or adjusted under 35 U.S.C. 154(b) by 0 days.

(21) Appl. No.: 10/475,394

(22) PCT Filed: Apr. 19, 2002

(86) PCT No.: PCT/NL02/00256

§ 371 (c)(1),
(2), (4) Date: Apr. 2, 2004

(87) PCT Pub. No.: WO02/085244

PCT Pub. Date: Oct. 31, 2002

(65) Prior Publication Data

US 2004/0154636 A1 Aug. 12, 2004

(30) Foreign Application Priority Data

Apr. 19, 2001 (NL) .................................. 1017883

(51) Int. Cl.
*A61C 15/00* (2006.01)
(52) U.S. Cl. .................................................. 132/323
(58) Field of Classification Search ........... 132/322, 132/323, 324, 325, 326, 327; D26/66, 67, D26/68; 223/99
See application file for complete search history.

(56) References Cited

U.S. PATENT DOCUMENTS

| | | | | |
|---|---|---|---|---|
| 122,241 A | * | 12/1871 | Farmer ......................... 223/99 |
| 1,287,926 A | * | 12/1918 | Ecaubert ...................... 132/325 |
| 1,608,212 A | * | 11/1926 | Hochstadter ................. 132/326 |
| 2,648,341 A | * | 8/1953 | Moll ............................ 132/323 |
| 2,682,126 A | * | 6/1954 | Shepherd .............. 269/254 CS |
| 2,784,722 A | | 3/1957 | Chamberlin et al. |
| 2,837,098 A | | 6/1958 | Sorboro |
| 3,393,687 A | | 7/1968 | Whitman |
| 3,472,247 A | | 10/1969 | Borsum et al. |
| 3,631,869 A | | 1/1972 | Espinosa |
| 3,718,146 A | | 2/1973 | Myers |
| 3,734,107 A | | 5/1973 | Thierman |
| 3,755,848 A | * | 9/1973 | Mutrie ......................... 15/184 |

(Continued)

FOREIGN PATENT DOCUMENTS

GB 2 122 495 A 1/1984

*Primary Examiner*—Todd E. Manahan
(74) *Attorney, Agent, or Firm*—The Webb Law Firm

(57) ABSTRACT

A method for cleaning teeth by drawing at least one cleaning thread in a reciprocating movement along teeth, at least one end of which cleaning thread is fastened to an elongate handling member, the other end of the thread is grasped with the hand, and the cleaning thread at least partially encircles the teeth during the movement. Thorough cleaning is hereby possible, so that the risk of teeth decay and/or gum disorders is avoided. The invention also relates to a device for cleaning teeth, comprising at least one elongate handling member with at least one opening formed close to an end of the member for passage of a cleaning thread, wherein the end of the member comprising the opening is adapted such that gums around the teeth are hereby not adversely affected. The device can be provided with means for holding the end of the handling member located opposite the opening, for instance in the form of a handle. The invention also relates to a handle for use in such a device.

21 Claims, 10 Drawing Sheets

U.S. PATENT DOCUMENTS

| | | | |
|---|---|---|---|
| 3,799,177 | A | 3/1974 | Bragg |
| 3,831,611 | A * | 8/1974 | Hendricks .................. 132/324 |
| 3,834,404 | A | 9/1974 | Chien |
| 3,881,502 | A * | 5/1975 | Bennington ................ 132/325 |
| 3,908,677 | A * | 9/1975 | Beach ........................ 132/325 |
| 3,939,853 | A | 2/1976 | Spanondis |
| 4,005,722 | A * | 2/1977 | Bragg ........................ 132/324 |
| 4,050,470 | A | 9/1977 | Miller |
| 4,214,598 | A | 7/1980 | Lee |
| 4,265,257 | A * | 5/1981 | Salyer ........................ 132/322 |
| D265,515 | S | 7/1982 | Levine |
| D272,565 | S | 2/1984 | Levine |
| 4,434,807 | A * | 3/1984 | Huskey ...................... 132/325 |
| D276,378 | S | 11/1984 | Levine |
| 4,920,993 | A * | 5/1990 | Mackie ...................... 132/324 |
| 4,926,820 | A | 5/1990 | Wearn |
| 5,085,236 | A * | 2/1992 | Odneal et al. .............. 132/325 |
| 5,170,809 | A | 12/1992 | Imai et al. |
| 5,224,502 | A | 7/1993 | Walker, Jr. |
| 5,323,796 | A | 6/1994 | Urso |
| 5,348,032 | A | 9/1994 | Mason |
| 5,406,965 | A | 4/1995 | Levine |
| D358,001 | S | 5/1995 | Ramsey |
| 5,450,866 | A * | 9/1995 | Wang et al. ................ 132/325 |
| 5,638,841 | A | 6/1997 | Levine |
| 5,657,780 | A * | 8/1997 | Giacopuzzi ................ 132/325 |
| 5,680,875 | A * | 10/1997 | Winters ...................... 132/324 |
| 5,692,532 | A * | 12/1997 | Gabrovsek ................ 132/325 |
| 5,735,299 | A * | 4/1998 | Kaltenbach ................ 132/323 |
| 5,762,079 | A * | 6/1998 | Protonantis ................ 132/325 |
| 5,842,490 | A * | 12/1998 | Jensen ...................... 132/309 |
| 6,019,109 | A * | 2/2000 | Moore ........................ 132/323 |
| 6,168,434 | B1 | 1/2001 | Böhm-Van Diggelen |

* cited by examiner

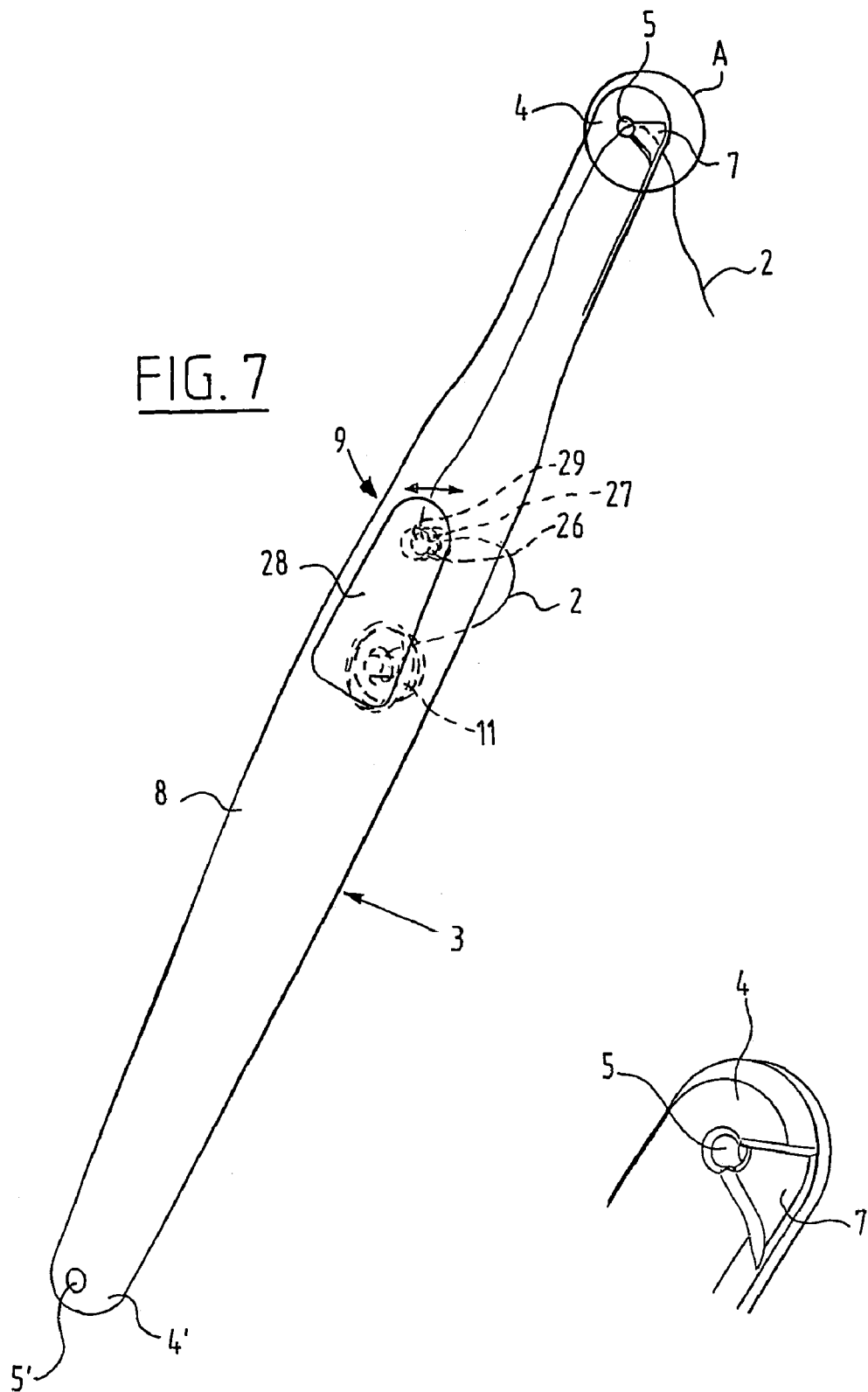

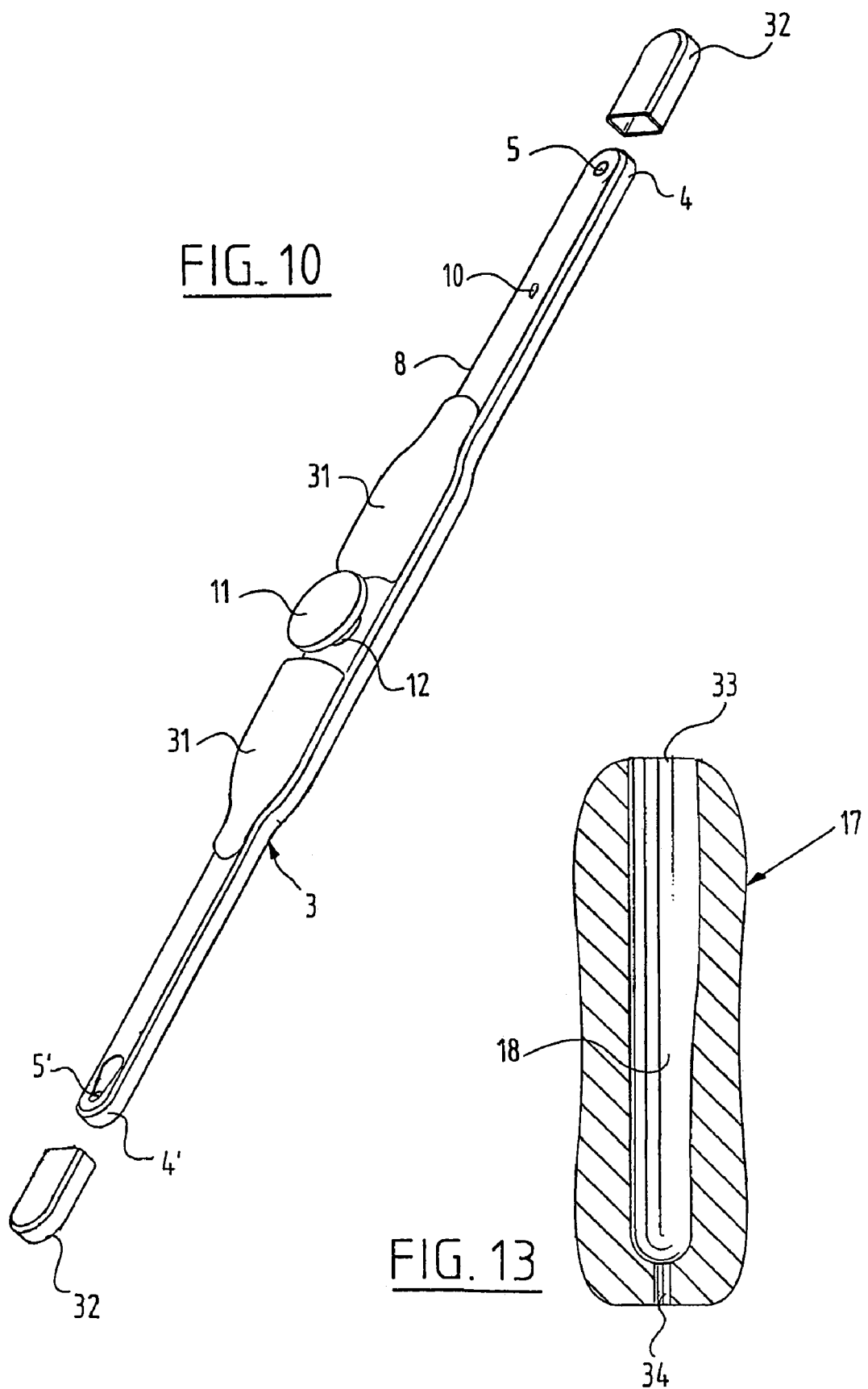

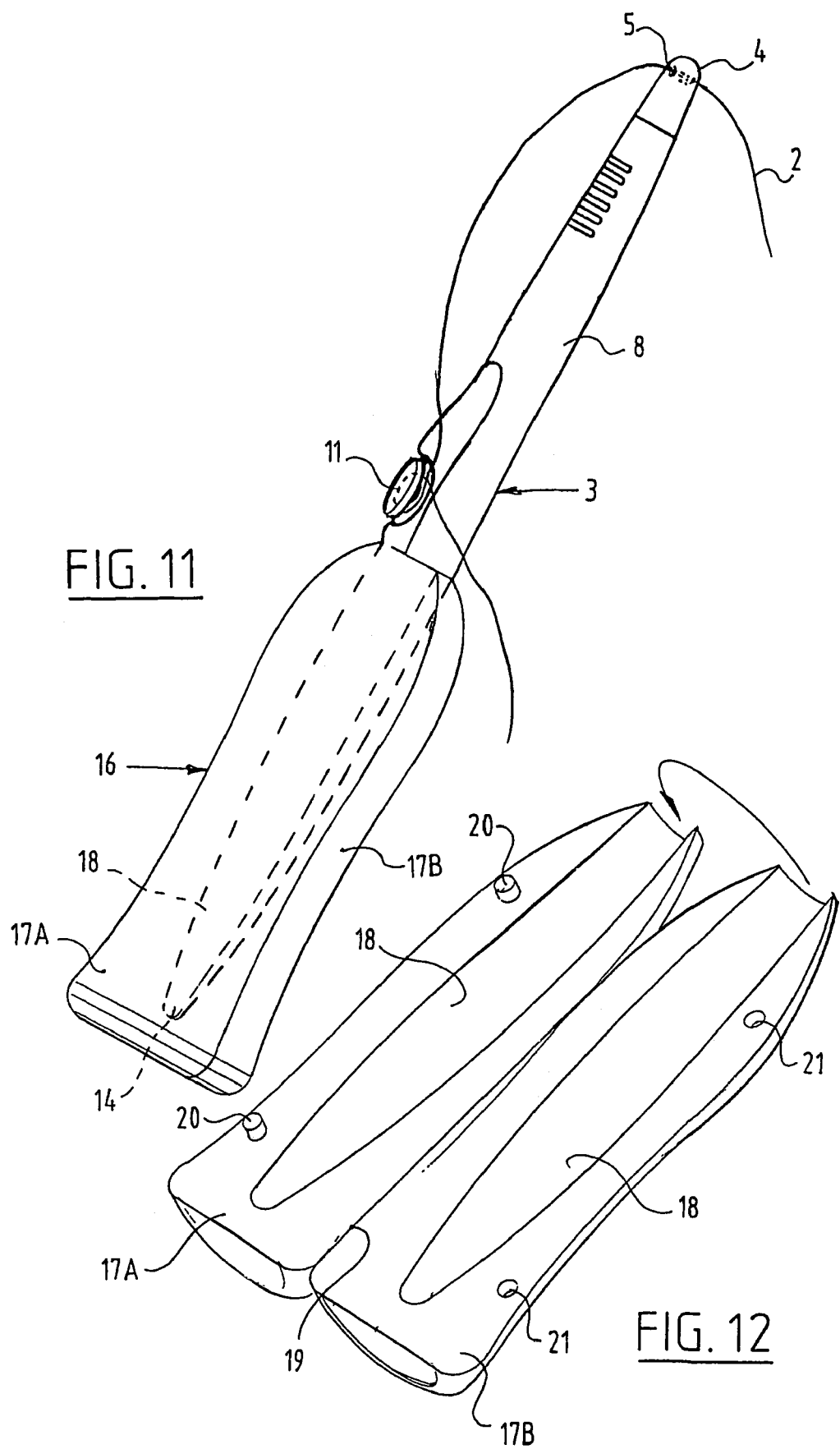

DEVICE FOR CLEANING TEETH

BACKGROUND OF THE INVENTION

1. Field of the Invention

The invention relates to a method and device for cleaning teeth.

2. Description of Related Art

It is generally known that regular cleaning of the teeth is a condition for preventing tooth decay and periodontitis. There are two common teeth-cleaning methods here, i.e. brushing and flossing.

Most widespread is brushing of the teeth using a toothbrush. Relatively large areas of the teeth can in general be adequately cleaned herewith. However, brushing with a brush is less suitable for cleaning of the spaces between the teeth and the gum line between teeth, while it is precisely in such spaces that food remnants will collect which can result in the occurrence of tooth decay and periodontitis.

It is per se known to clean these spaces using a special, very narrow and sharp toothbrush, a so-called interdental brush. The use of such an interdental brush can however easily result in damage and/or inflammation of the gums. This is particularly the case when the spaces for cleaning are small, as will be case with young people.

Flossing is therefore especially suitable for cleaning the spaces between teeth and the gum line between teeth. A thin thread is herein moved reciprocally between the teeth and round the necks of the teeth. The problem with flossing is that it is a relatively complicated operation which is often only carried out reluctantly. Flossing, in contrast to brushing, is moreover not simple to perform with an electrical appliance.

Different aids have already been proposed with which the flossing treatment can be simplified. Such an aid in which all the measures of the preamble of claim 3 are combined is for instance described in U.S. Design Pat. No. D 358,001. The cleaning tool described therein consists of two sticks, between the ends of which a floss thread is spanned. In order to fasten the floss thread, the ends of the floss sticks are each provided with a protruding end disc. This involves the risk of damaging the gums. Furthermore, a new length of floss thread has to be spanned between the sticks at every use, which is awkward and time-consuming work. Finally, the floss thread is not easy to release in such a device if it becomes stuck.

Known from U.S. Pat. Nos. 4,050,470 and 4,926,820 are aids which consist of two elongate members between which a length of thread can be spanned. These aids have the drawback that a user must always reach into his/her mouth with a hand. There is also the drawback with these aids that a floss thread stuck between the teeth cannot be easily released.

Further known from U.S. Pat. Nos. 3,799,177 and 5,323,796 are electrically driven flossing devices which consist of a handle with a drive therein and two arms protruding therefrom between which a flossing thread is movable. A manually operated variant of these devices is described in U.S. Pat. No. 4,214,598. All these Y-shaped or U-shaped devices have the drawback that a floss thread which is stuck cannot be released quickly, while the devices are moreover relatively large and so cannot be readily placed into the mouth. In addition, there is also the risk, as a result of the often unstable construction of these devices, that they make unintended movements, which could result in injury to the mouth.

SUMMARY OF THE INVENTION

The invention now has for its object to provide a method with which teeth can be cleaned in rapid and simple manner, in addition to a device with which this method can be performed.

A method for cleaning teeth by drawing at least one cleaning thread in a reciprocating movement along teeth, so-called flossing, is characterized according to the present invention in that at least one end of the cleaning thread is fastened to an elongate handling member, the other end of the thread is grasped with the hand, and the cleaning thread at least partially encircles the teeth during the movement. By not grasping one end of the thread, which has to be moved reciprocally in the oral cavity, with the hand but fastening it to an elongate handling member, a very hygienic method is obtained. The method is hereby also suitable for application by carers of people who are themselves not able to floss. The use of a handling member further makes it possible to carry out a movement wherein the cleaning thread at least partially encircles the necks of the teeth on both the inside and outside. Because the handling member is furthermore elongate and therefore relatively thin, it can be readily placed in the mouth and moved reciprocally therein without the mouth having to be opened very wide. Through the use of only one handling member there is further no risk of the floss thread remaining stuck between two teeth, since the end held with the hand can after all always be pulled out.

It is on the other hand also possible for each end of the cleaning thread to be fastened to an associated elongate, handling member, wherein the fastening of one of the ends is releasable. The use of the hands can thus be avoided altogether, wherein there are still no problems when the thread becomes stuck.

The invention also relates to a device with which the above described method can be performed. Such a cleaning device, which in conventional manner comprises an elongate handling member, with at least one opening formed close to an end of the member for passage of a cleaning thread, has the feature according to the invention that at least the end of the member comprising the opening is adapted such that gums around the teeth are hereby not adversely affected. By thus embodying the end of the handling member, damage to the gums, and thereby the occurrence of inflammations and the like, can be prevented if the handling member unintentionally comes into contact with the gums.

According to a first embodiment of the cleaning device, the end comprising the opening is herein manufactured from or covered with a relatively soft material. The chance of injuries occurring is hereby small. A device which is simple to manufacture and durable is herein obtained when the relatively soft material is a plastic, in particular an elastomer.

According to another embodiment of the cleaning device, the end comprising the opening can additionally or alternatively take a relatively narrow form. The chance of the end unintentionally coming into contact with the gums is hereby relatively small.

Advantageously the end comprising the opening can further be rounded off, whereby this end will not penetrate into the gums but will as it were glance off them.

In order enable guiding of the cleaning wire in reliable manner along the end of the handling member, the opening is preferably bounded by a peripheral edge closed on all sides, so that the thread cannot escape therefrom. In order to reduce wear on the thread and to enable the thread to be pulled a length further in simple manner, the peripheral edge is advantageously substantially circular. However, the peripheral edge can herein have a gap-like tapering portion in which the thread can be clamped.

Conversely, the opening can be formed by an incision with constricted portion in an edge of the handling member. The cleaning thread can hereby be placed relatively quickly and easily into the opening or removed therefrom.

In both cases means can be provided for guiding the cleaning thread to the opening, which guide means can be formed by a part of the handling member tapering toward the opening. The thread can thus always be placed in the opening in simple manner.

The cleaning device can be further provided with means connected to the handling member for fixing the cleaning thread. In a simple embodiment of the device these fixation means can comprise at least one incision formed in the vicinity of the opening in an edge of the handling member, although an embodiment which is very simple to operate is obtained when the fixation means comprise at least one clamping element connected movably to the handling member.

There can also be provided means connected to the handling member for severing the cleaning thread, for instance in the form of a sharp cutting edge. This edge could be formed in the handling member or a blade could be fixed to the member. The cutting means can also be accommodated in a protective cap for arranging detachably over a part of the handling member.

In addition, the cleaning device is advantageously provided with means connected to the handling member for storing a supply of cleaning thread. These storage means can comprise at least one spool arranged on the handling member. This is particularly advantageous because different manufacturers of cleaning thread supply their product on spools. Such a spool could then be readily mounted—for instance releasably—on the handling member. For thread supplied in loose form or in balls the storage means can comprise at least one receiving space formed in the handling member.

The handling member is in principle intended to be grasped by the user. For users who for whatever reason have difficulty with holding the relatively thin handling member, the cleaning device can be equipped with means for grasping the end of the handling member located opposite the end comprising the opening.

According to a first variant, these holding means comprise a coupling for connection to a handle of an electrical appliance, for instance an electric toothbrush. Such a handle is usually quite sizeable and therefore easy to handle, while an electric toothbrush is already present anyway in most households.

According to another variant, the holding means comprise a handle with a recess fitting closely round the end of the handling member. If the handle is substantially tubular, with an insertion opening on a first side and an outlet opening on an opposite side, this is cheap and simple to manufacture, for instance from a foam plastic. In order that the handling member can be readily received in the handle, this latter can have two parts connected movably to each other, whereby it can be opened and closed. In that case the handle can be manufactured from a rigid material, for instance a hard plastic or even a metal, and the recess can optionally be covered with a soft and rough material.

The invention finally also relates to a handle evidently intended for application in a cleaning device as described above.

BRIEF DESCRIPTION OF THE DRAWINGS

FIG. 7 is a perspective view of a third embodiment of the handling member, according to the present invention;

FIG. 10 is a perspective view of a fifth embodiment of the handling member, according to the present invention;

FIG. 11 is a perspective view of an example of a handling member received in a handle, according to the present invention;

FIG. 12 is a perspective view of the handle of FIG. 11 in folded open position, according to the present invention;

FIG. 13 is a cross-sectional view through an alternative embodiment of the integral handle, according to the present invention.

DETAILED DESCRIPTION OF THE INVENTION

In a method according to the invention for cleaning teeth, a cleaning thread is drawn in a reciprocating movement along teeth such that the thread as it were "hugs" the teeth. This cleaning treatment, known as flossing is performed in conventional manner by spanning a cleaning thread or floss thread between both hands and then working the thread between teeth and moving it reciprocally. The necks of the teeth and the interdental spaces in particular can be properly cleaned in this manner.

Because moving the thread reciprocally in the mouth using one or more fingers is perceived by many people as unpleasant or at least unhygienic, it is proposed according to the invention to fasten one end of thread 2 to an elongate handling member 3 which is held in one of the hands 1 of a user. The other end of thread 2 is then grasped in conventional manner in the hand. This has the advantage that only the elongate handling member is placed in the mouth and has to be moved reciprocally therein, whereby it is not necessary to open the mouth wide. The treatment is thereby not perceived as so very unpleasant, while it also becomes accessible for people who cannot open their mouth very far. In addition, the use of a handling member 3 is attractive to people who have to clean the teeth of others, such as nursing staff, parents and the like. Furthermore, thread 2 can in this way be drawn in an "embracing" movement along the teeth.

Figure 1:
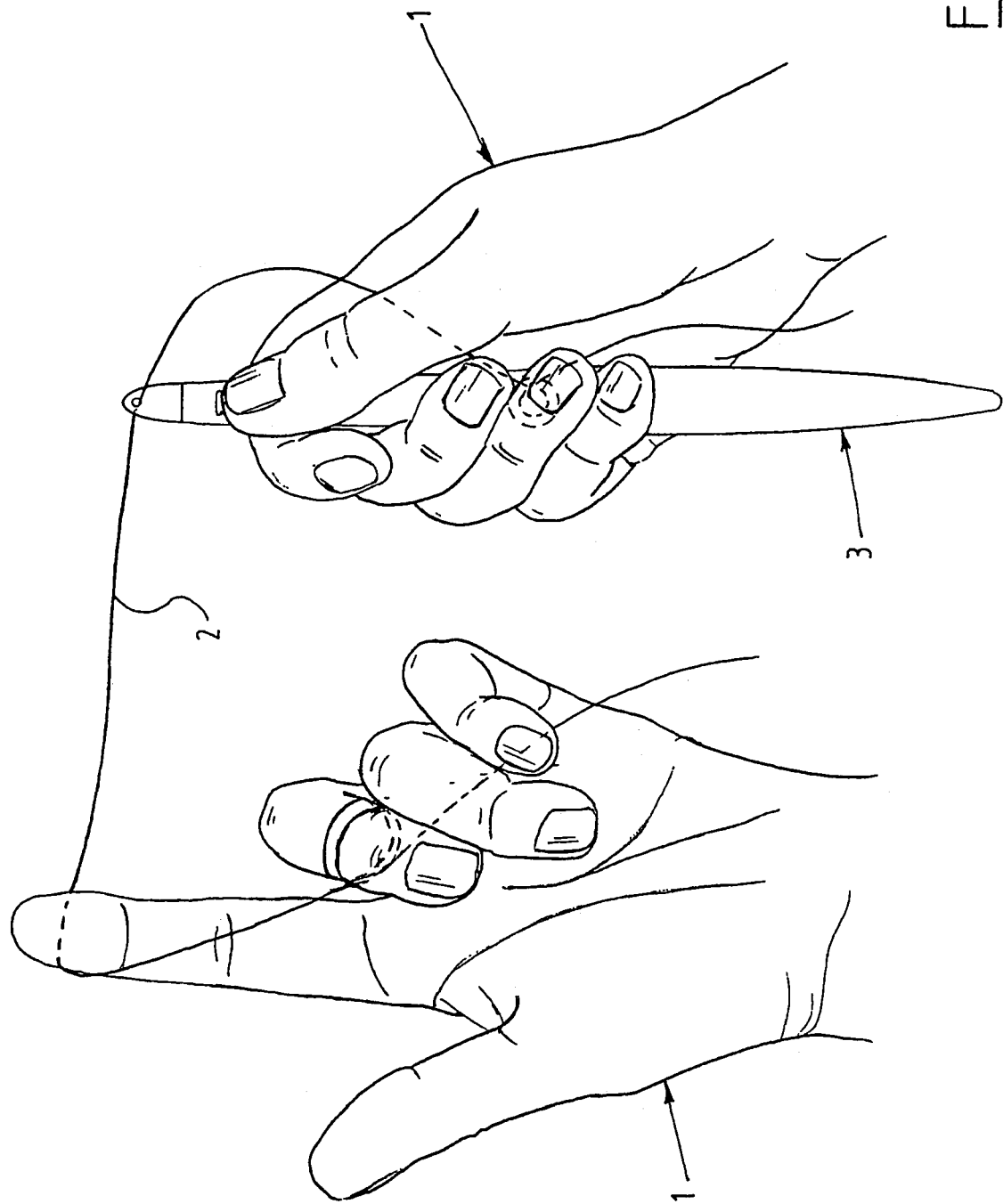
FIG. 1 is a schematic view of a possible method of spanning a cleaning thread in a handling member for application of the method, according to the present invention.
Figure 4:
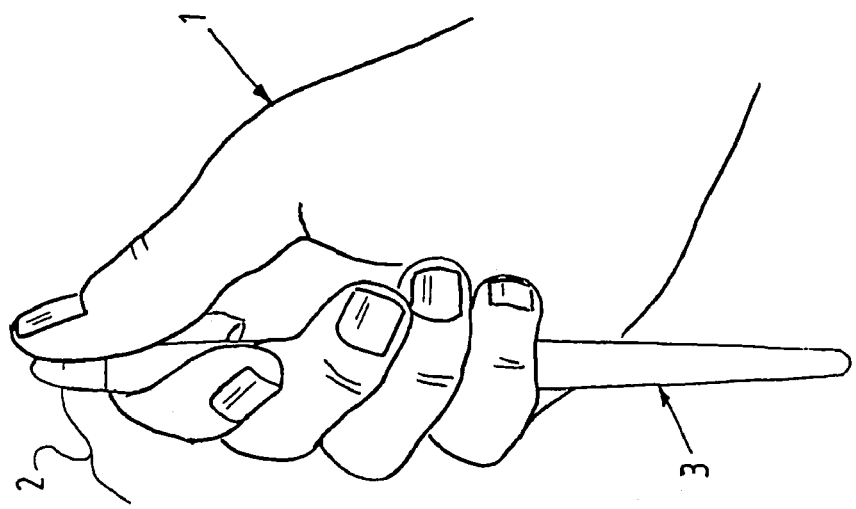
FIGS. 2-4 are schematic views of further ways of holding the handling member, according to the present invention.
Figure 3:
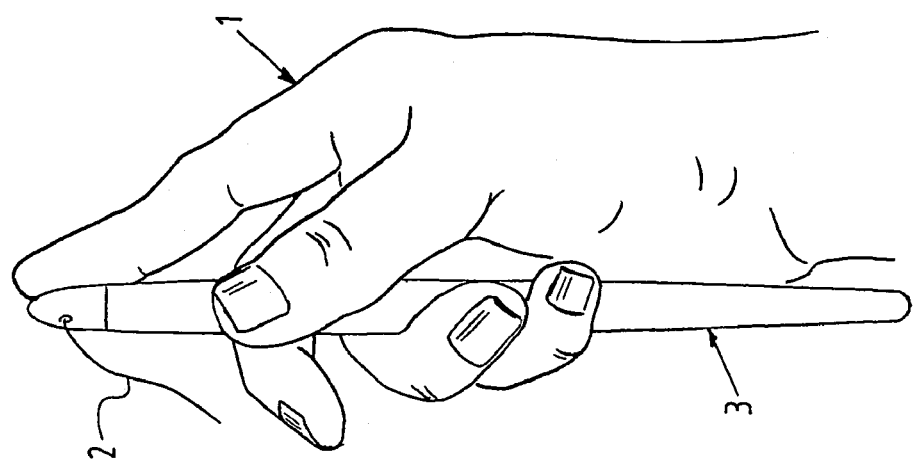
Figure 2:
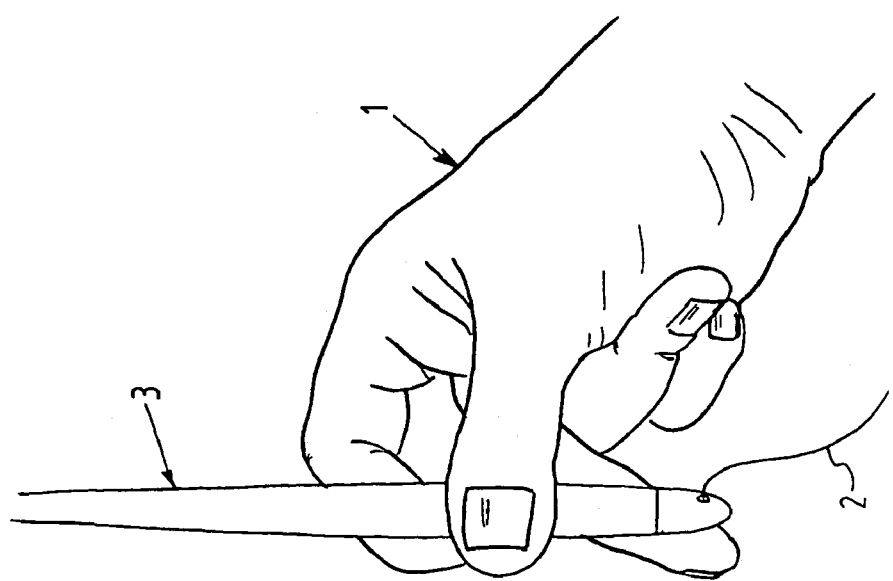

Handling member 3 can otherwise be grasped in different ways, partly depending on the position of the teeth for cleaning (in the upper jaw or lower jaw). Cleaning thread 2 can thus be clamped with the middle finger (FIG. 2), the index finger (FIG. 3) or the thumb (FIG. 4).

The handling member 3 has on at least one end 4 an opening 5 through which the cleaning thread 2 can be carried. According to the invention this end 4 of handling member 3 is in any case adapted such that the gums around the teeth of the user are thereby not adversely affected. One option for this purpose is to manufacture this end 4 from a relatively soft material, for instance a plastic such as an elastomer. This prevents contact of the end 4 with the gums resulting directly in injury to the gums. It is of course also possible to cover this end 4 with a layer of the relatively soft material. The shank 8 of handling member 3 can then be formed from a relatively hard and smooth material, for instance a hard plastic or a metal, to enable easy cleaning thereof.

Additionally or alternatively, the end 4 in which the opening 5 is arranged can be given a relatively narrow form, thereby reducing the chance of this end 4 unintentionally coming into contact with the gums. It is also recommended to round off this end 4 so that it will not cut into the gums.

In most of the embodiments shown here there are otherwise openings 5, 5' with different diameters formed on both ends 4, 4' of handling member 3. The thickness of the ends 4, 4' can also differ herein. The thicker end 4' with the larger opening 5' therein is then particularly suitable for use by adults, who will after all have a larger mouth than young people but who will also have more difficulty with inserting the thread 2 into the small opening 5. The thinner end 4 with small opening 5 is intended for use by young people.

Figure 5A:
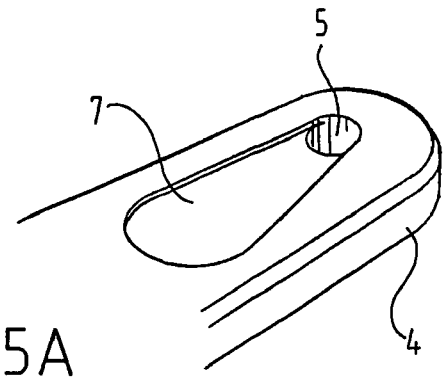
FIGS. 5A and 5B are detail views on enlarged scale of ends of the handling member of FIG. 5.
Figure 5:
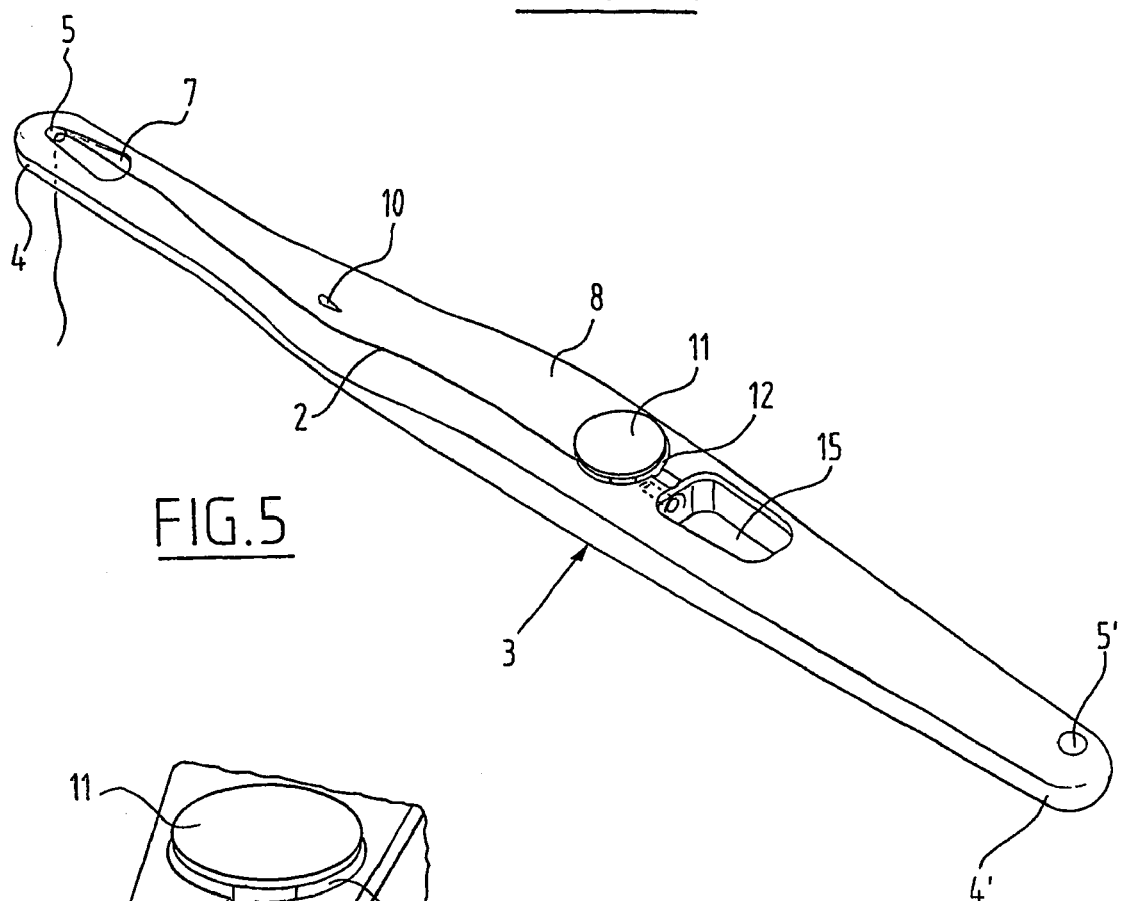
FIG. 5 is a perspective view of a first embodiment of the handling member with cleaning thread, according to the present invention.
Figure 5B:
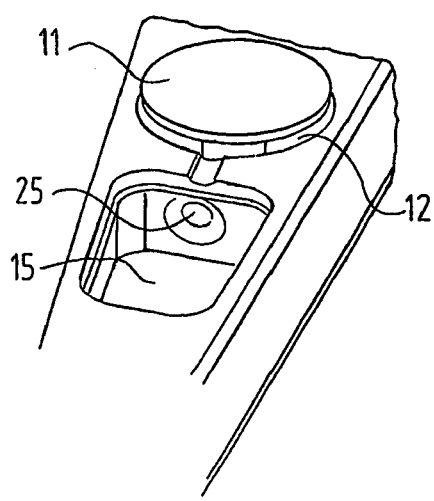

In order to grasp cleaning thread 2 as well as possible the opening 5 can be bounded by a peripheral edge 6 which is closed on all sides (FIG. 5A). This peripheral edge 6 is herein substantially circular to limit wear of the thread as much as possible, but can also have a gap-like, tapering portion (not shown here) in which thread 2 can be clamped.

In order to enable simpler insertion of thread 2 into the small opening 5, there are provided guide means 7 which are formed here by a recess in the surface of shank 8 which tapers in the direction of opening 5. So as not to obstruct the movement of thread 2 to the opening, the end 4 of the handling member is in this case manufactured from a relatively smooth and hard material.

In addition, handling member 3 has in the shown embodiment means 10 for severing a used length of cleaning thread. These cutting means 10 here take the form of a protruding triangular part with cutting edges which is arranged on shank 8. This cutting part 10 can be manufactured from a material other than that of shank 8, for instance a metal. It is however also possible to envisage embodying the cutting means in the form of a groove with sharp edges formed in shank 8.

In order to enable simple storage of a supply of cleaning thread, handling member 3 is provided with means for storage thereof. In the shown embodiment these storage means take the form of a spool 11 which is here accommodated in a recess 12 which is in turn formed in a thickened portion of the handling member. This thickened portion results in the handling member 3 being easy to grasp. In addition, the storage means comprise a receiving space 15 which communicates with recess 12 via a channel 25. In this receiving space 15 can be stored a ball of thread 2 which is then guided via channel 25 to spool 11, and from there to one of the openings 5, 5'. When thread 2 is trained a few times around spool 11 it is held fast, so that spool 11 also functions as fixation means. Spool 11 can otherwise be releasable so that it can be replaced in simple manner when the supply of thread 2 is exhausted.

Figure 6:
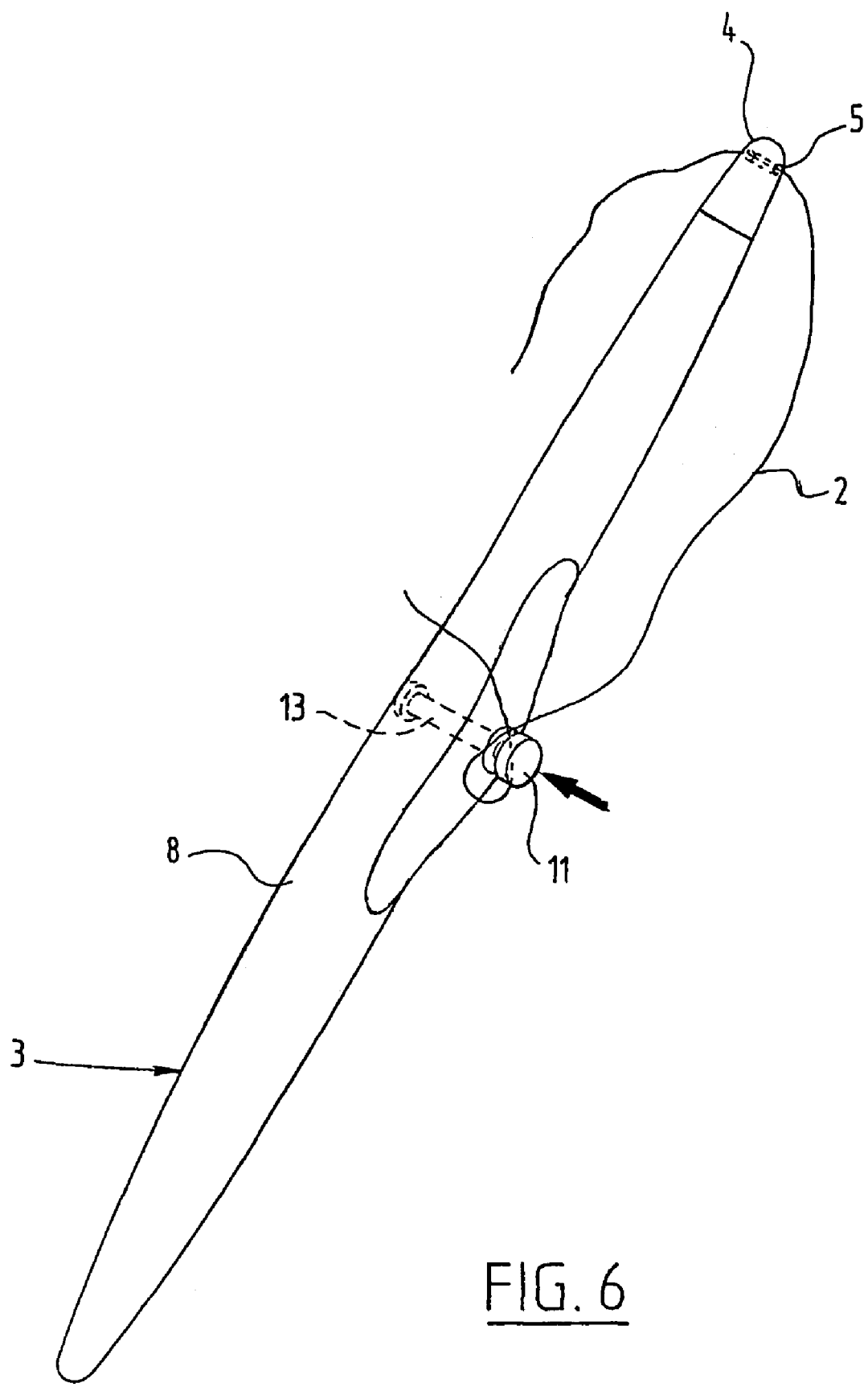
FIG. 6 is a perspective view of a second embodiment of a handling member with cleaning thread, according to the present invention.

In an alternative embodiment of handling member 3 (FIG. 6) the spool 11 is arranged on a shaft 13 extending through the shank 8 of the handling member. By now pressing spool 11 firmly against shank 8 the part of thread 2 trained therearound is clamped, whereby here too the storage means 11 thus function directly as fixation means.

Yet another embodiment of handling member 3 (FIG. 7) is provided with fixation means 9 in the form of a movable clamping element 28. In this variant the guide means 7 are formed by a recess which extends from an edge of handling member 3 to the small opening 5. Storage spool 11 is here situated on the opposite side of shank 8, and thread 2 is guided from this spool through a channel 26. Channel 26 runs out into a funnel-shaped mouth 27 which can be closed by a plug-like end part 29 of clamping element 28. This clamping element 28 can be formed integrally with the shank 8 and owing to its small thickness can be resiliently flexible, so that it can be readily pressed in to fix thread 2 in funnel-shaped mouth 27.

Figure 8A:
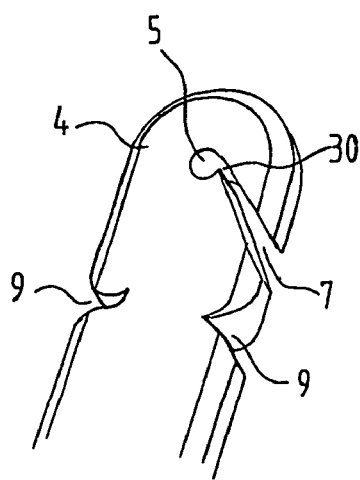
FIG. 8A is a detail view on enlarged scale of an end of the handling member of FIG. 8.

Although an opening 5 with a peripheral edge 6 closed on all sides holds cleaning thread 2 optimally, it may be desirable, with a view to rapid drawing of thread 2 through the opening, to embody this opening 5 as a gap or incision open on one side (FIG. 8A). Opening 5 must be sufficiently large to enable thread 2 to be moved back and forth in simple manner therethrough. However, in order to prevent thread 2 coming loose from opening 5, the incision is preferably provided with a constricted portion 30, the width of which roughly corresponds with the thickness of thread 2. Guide means 7 are herein then embodied in the form of a relatively wide mouth of the incision 5 which tapers toward the constriction 30 and through which the thread 2 can be readily inserted. Additional incisions can herein be formed in the edge of shank 8 as fixation means 9. A small spool 11 can also be formed for storing or fixing a length of thread.

In yet another embodiment of handling member 3 (FIG. 10), shank 8 is relatively flat and embodied in a smooth and hard material, and elevated gripping means 31 of a softer and rougher material are formed thereon. Formed between these elevated parts 31 is another recess 12 in which the spool 11 is arranged. In this embodiment protective caps 32 are further pushed over both ends 4, 4', whereby openings 5, 5' are protected from contamination when handling member 3 is not in use. A knife (not shown) can then for instance be arranged in one of these caps 32 for severing the cleaning thread 2 after use.

Figure 8:
FIG. 8 is a perspective view of a fourth embodiment of the handling member, according to the present invention.
Figure 9:
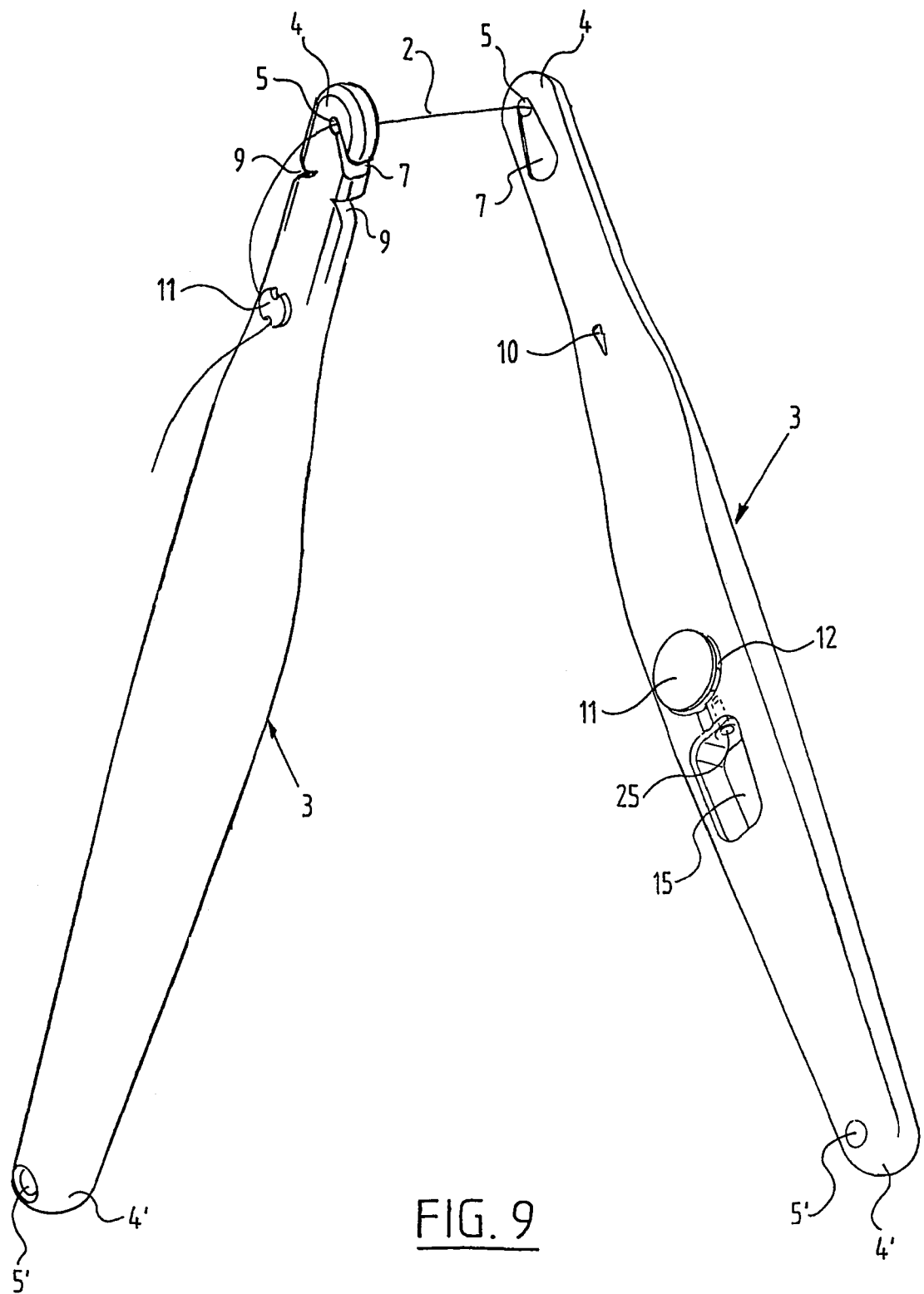
FIG. 9 is a perspective view illustrating the use of two handling members, according to the present invention.
Figure 14:
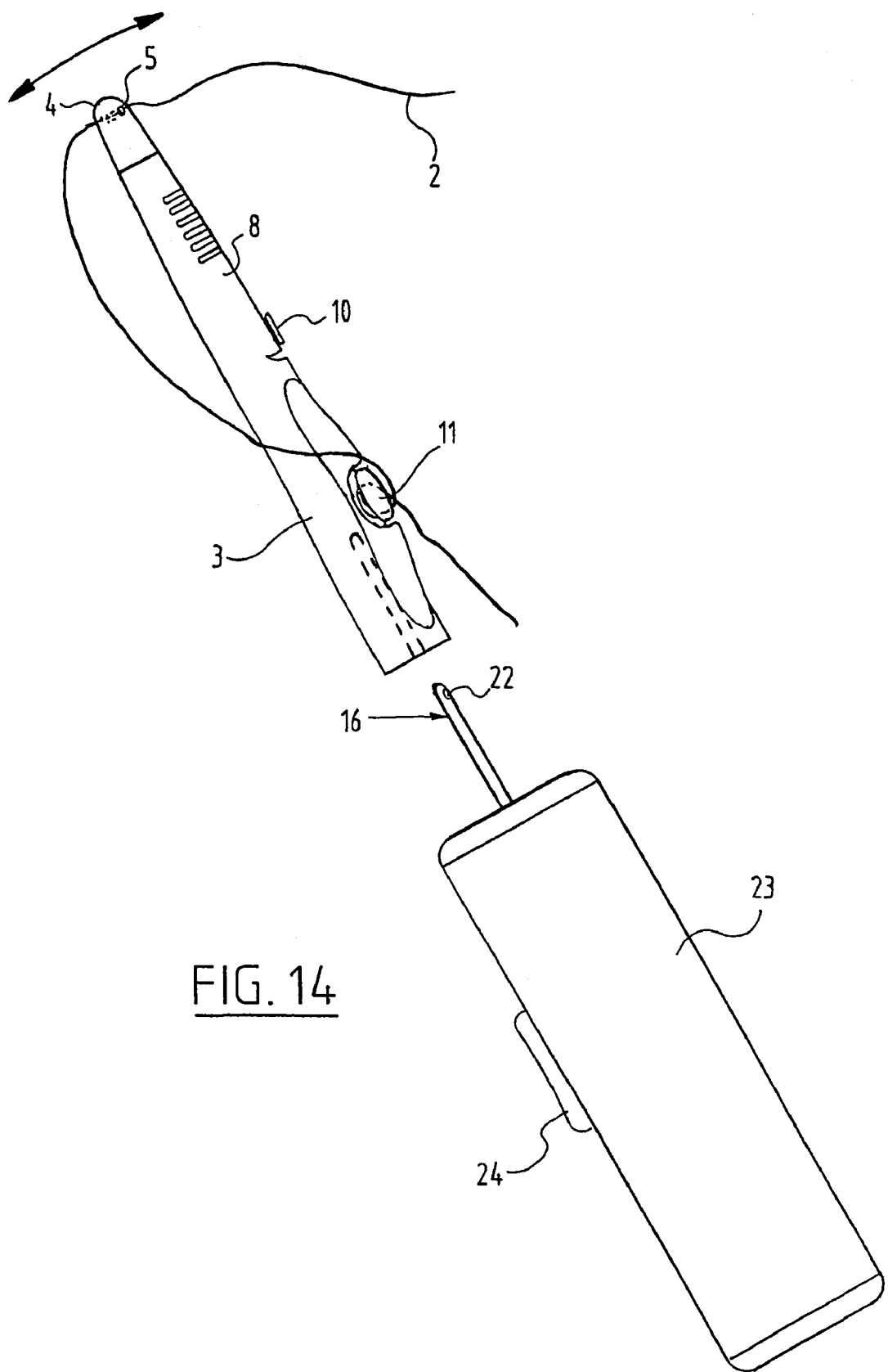
FIG. 14 is a perspective view of an embodiment wherein the handling member is pushed onto the handle of an electric toothbrush.

Although the method according to the invention is applied most simply by fastening only one end of thread 2 to a handling member 3 and taking the other end in the hand, the use is not precluded of two handling members 3 between which the thread 2 is spanned if for one reason or another a user finds this convenient. It is then recommended here that one of the two handling members 3 used is provided with a gap-like opening 5 as shown in FIG. 8 in order to allow easy release of thread 2 in the unlikely event it becomes stuck in the teeth of the user.

With a view to placing thereof in the mouth, handling member 3 must be as slender as possible. For convenience of use however, a very slender form is not always an advantage. Particularly elderly people and people with motor problems often have difficulty in firmly grasping a very slender object. Means can in that case be provided for grasping the end 14 lying opposite the end 4 with the opening 5, which holding means 16 then have a larger diameter than the slender handling member 3 itself.

In a first embodiment the holding means 16 are formed by a handle 17 (FIGS. 11, 12) which has a recess 18 in which the end 14 of handling member 3 is received in close-fitting manner. In the shown embodiment the handle 17 comprises two parts 17A and 17B which are movably connected to each other and which can for instance be connected by a film hinge 19. Means can herein be provided for fixing the two halves 17A, 17B in the closed position, for instance in the form of pins 20 and corresponding openings 21 in the two halves 17A, 17B.

Conversely, handle 17 can of course also be manufactured integrally (FIG. 13), wherein handling member 3 is then simply pressed from one side through an insertion opening 33 into recess 18. An outlet opening 34 is in that case provided on the opposite end to prevent moisture and contamination accumulating in recess 18.

Handle 17 can be manufactured from many different materials. If it takes a tubular form, the force for clamping the handling member 3 therein must be generated through deformation, so that handle 17 can then be made from a readily deformable material such as foam plastic. It is however also possible to manufacture handle 17 from a hard material and to form the recess 18 precisely in accordance with the member for receiving therein. Handle 17 can for instance be shaped around the member and then fixed into this shape by adding a hardener.

In another embodiment the holding means 16 are formed by a coupling 22 with which handling member 3 can be connected to handle 23 of an electric toothbrush. Such a handle is usually relatively thick and heavy because the power supply and the motor of the electric toothbrush are arranged therein, as well as a control switch 24.

Although the invention is elucidated above on the basis of a number of embodiments, it will be apparent to the skilled person that it is not limited thereto. Many other configurations of the handling member with and without storage means, cutting means, fixation means and the like can thus be applied. It is for instance possible to provide a cleaning device which is suitable for both flossing and brushing. This can be done by providing the end of the handling member opposite the end with the opening with a normal or interdental brushing head. The measures for protecting the gums from the end of the handling member, i.e. the choice of material, design and dimensioning of this end, can be applied separately or in combination. The embodiment of the handle can also be varied in many ways. In the case of a tubular handle a large number of handles could thus be formed together as tube and then separated from each other by cutting along a separating line. In addition, the holding means, in particular handle 17 with recess 18, can also be applied in combination with cleaning means other than the shown handling member, for instance a conventional toothbrush or an interdental brush, or even in combination with other tools for holding in the hand, such as cutlery, household products and so on.

The scope of the invention is therefore defined solely by the appended claims.

The invention claimed is:

1. A cleaning device for cleaning teeth, comprising at least one elongate handling member with at least one opening formed close to an end of the member for passage of a cleaning thread, the opening extending from one side of the handling member to an opposite side thereof, wherein at least the end of the member comprising the opening is adapted, such that gums around the teeth are hereby not adversely affected, the device further comprising means connected to the handling member for storing a supply of cleaning thread and means for guiding the cleaning thread to the opening, wherein the storage means comprise at least one spool, wherein a portion of the spool is arranged on an outer surface of the handling member perpendicular to a lengthwise axis of the handling member, and wherein the guide means comprise a recess tapering toward the opening in the surface of the handling member.

2. The cleaning device as claimed in claim 1, wherein the end comprising the opening is manufactured from or covered with a substantially soft material.

3. The cleaning device as claimed in claim 2, wherein the soft material is a plastic.

4. The cleaning device as claimed in claim 3, wherein the soft material is an elastomer.

5. The cleaning device as claimed in claim 1, wherein the end comprising the opening is in a substantially narrow form.

6. The cleaning device as claimed in claim 1, wherein the end comprising the opening is rounded.

7. The cleaning device as claimed in claim 1, wherein the opening is bounded by a peripheral edge closed on all sides.

8. The cleaning device as claimed in claim 1, wherein the opening is formed by an incision with constricted portion in an edge of the handling member, and the guide means form a widened neck of the incision tapering toward the constricted portion.

9. The cleaning device as claimed in claim 1, further comprising means connected to the handling member for fixing the cleaning thread.

10. The cleaning device as claimed in claim 9, wherein the fixation means comprise at least one incision formed in the vicinity of the opening in an edge of the handling member.

11. The cleaning device as claimed in claim 9, wherein the fixation means comprise at least one clamping element connected movably to the handling member.

12. The cleaning device as claimed in claim 1, further comprising means connected to the handling member for severing the cleaning thread.

13. The cleaning device as claimed in claim 1, wherein the storage means comprise at least one receiving space formed in the handling member.

14. The cleaning device as claimed in claim 1, wherein an opening is formed close to each of the ends of the handling member, and both openings have different diameters.

15. The cleaning device as claimed in claim 1, further comprising means for grasping the end of the handling member located opposite the end comprising the opening.

16. The cleaning device as claimed in claim 15, wherein the holding means comprise a coupling for connection to a handle of an electrical appliance.

17. The cleaning device as claimed in claim 15, wherein the holding means comprise a handle with a recess fitting closely round the end of the handling member.

18. The cleaning device as claimed in claim 17, wherein the handle has two parts connected movably to each other.

19. The cleaning device as claimed in claim 17, wherein the handle is substantially tubular with an insertion opening on a first side and an outlet opening on an opposite side.

20. A cleaning device for cleaning teeth, comprising:
   an elongate handling member having a relatively wide and thick central portion and at least one relatively narrower and thinner end, a substantially circular opening being formed close to said relatively narrower and thinner end of the member for the passage of a cleaning thread from one side of the member to an opposite side;

storage means connected to the handling member for storing a supply of cleaning thread, said storage means comprising at least one spool arranged in a recess formed in the relatively wide and thicker central portion, said spool protruding substantially perpendicular to a lengthwise axis of the handling member;

guide means for guiding the cleaning thread to the opening, said guide means comprising a tapered recess formed in the surface of the handling member adjacent the opening; and severing means connected to the handling member for severing the cleaning thread.

21. The cleaning device as claimed in claim 20, wherein the severing means include a groove formed in said handling member and having sharp edges.

* * * * *